United States Patent [19]

Stiefel et al.

[11] Patent Number: 4,681,635
[45] Date of Patent: Jul. 21, 1987

[54] TOPICAL COLLODION COMPOSITIONS

[75] Inventors: Werner K. Stiefel, Coral Gables, Fla.; Charles F. Breunig, Greenville, N.Y.

[73] Assignee: Stiefel Laboratories, Inc., Coral Gables, Fla.

[21] Appl. No.: 846,362

[22] Filed: Mar. 31, 1986

[51] Int. Cl.$^4$ ............................ C08L 1/08; C08L 1/18
[52] U.S. Cl. .................................... 106/178; 106/195
[58] Field of Search ................................ 106/195, 178

[56] References Cited

U.S. PATENT DOCUMENTS 2,798,058  7/1957  Barber et al. ..................... 524/555

OTHER PUBLICATIONS

Stiefel Lab, "Duofilm", product insert, Mar. 1985.

*Primary Examiner*—Theodore Morris
*Attorney, Agent, or Firm*—Bruce M. Collins

[57] ABSTRACT

The drying time of fluid collodion topical compositions can be decreased without significant increase in overall viscosity through the incorporation of D,L-lactic acid.

5 Claims, No Drawings

TOPICAL COLLODION COMPOSITIONS

DETAILED DESCRIPTION

The present invention pertains to improved collodion composition intended for topical application. Collodion compositions are widely employed in human and veterinarian applications as topical protectants. USP specifications call for a solution of nitrocellulose in ether and alcohol, typically 4 parts by weight of nitrocellulose dissolved in 75 parts by volume of ethyl ether and 25 parts by volume of ethanol. The resultant product is a syrupy liquid, generally pale yellow in color, which when applied to the skin and exposed to air forms a tough, colorless film.

Although collodion itself can be used as a skin protectant, various therapeutic agents often are added, as for example, tannic acid, salicylic acid, cantharides, camphor, etc.

Since the therapeutic use of collodion preparations depend upon the formation of a protective film, the drying or film forming time following application should be brief as possible. The addition of components to accelerate drying, however, should not adversely effect the viscosity of the fluid material since an excessive increase in viscosity renders more difficult the application of the composition.

The present invention is based upon the discovery that the addition of D,L-lactic acid to collodion compositions will reduce significantly their drying time and that this can be accomplished without adverse effect on the overall viscosity of the composition. Moreover, D,L-lactic acid is sufficiently soluble in the organic solvents of collodion compositions that an amount up to and in excess of 20% by weight can be added.

The ability of the D,L-lactic acid to accelerate the drying time of collodion compositions significantly is not shared by closely related compounds. Hence closely related hydroxycarboxylic acids such as malic acid, citric acid and tartaric acid either do not produce the same effect on drying time, or significantly increase viscosity (or both). Even utilization of L-lactic acid fails to produce the same effect over the entire range.

Preparation of the improved formulation is achieved by dissolving the desired amount of D,L-lactic acid in a conventional collodion formulation. The quantity of D,L-lactic acid which is added will be at least that amount which significantly increases the drying time without adversely effecting the viscosity of the formulation. Generally this will be from about 5% to about 20%, preferably from about 15% to 20%. The resulting product is then utilized in the same fashion as known collodion preparations.

The following examples will serve to further typify the nature of this invention.

EXAMPLE 1

A flexible collodion composition is prepared by dissolving eight parts by weight of pyroxylin (chiefly nitrocellulose) in 50 parts by volume of ethanol and 150 parts by volume of ethyl ether. To this simple collodion preparation is added 2% by weight of camphor and 3% by weight of castor oil, the resulting flexible collodion formulation containing about 67% ether and about 22% alcohol by volume.

The viscosity of the composition (22° C., spindle No. 1, 30 rpm) is 84 cps. When exposed to air the drying time is 12 minutes.

To the above composition is added 16.5% by weight of D,L-lactic acid which is thoroughly dissolved therein. The viscosity of the final product is virtually unchanged, 78 cps, but the drying time when exposed to air is 4.5 minutes, a reduction of 62%.

EXAMPLE 2

In a series of tests, various organic acids were added to a flexible collodion preparation as disclosed above. The viscosity of the final material and the drying times are shown on the following table:

|  | Drying Time (minutes) | Percent Reduction | CPS | Percent Increase |
|---|---|---|---|---|
| Control | 12 | — | 84 | — |
| D,L-Lactic Acid | | | | |
| 5% | 6.5 | 46% | 96 | +14% |
| 10% | 7.5 | 38% | 86 | +2% |
| 15% | 5.5 | 54% | 81 | −4% |
| 20% | 7.5 | 38% | 88 | +4% |
| L-Lactic Acid | | | | |
| 5% | 10 | 16% | 108 | +28% |
| 10% | 12 | 0% | 102 | +21% |
| 15% | 13 | −8% | 105 | +25% |
| 20% | 9 | 25% | 114 | +35% |
| Malic Acid | | | | |
| 5% | 12 | 0% | 111 | +32% |
| 10% | 11 | 8% | 128 | +52% |
| 15% | 13 | −8% | 126 | +50% |
| 20% | 13.5 | −13% | 200 | +138% |
| Citric Acid | | | | |
| 5% | 7 | 42% | 108 | +28% |
| 10% | 8.5 | 29% | 103 | +22% |
| 15% | 16 | −33% | 180 | +114% |
| 20% | * | * | * | * |
| L-Tartaric Acid | | | | |
| 5% | 11 | 8% | 144 | +71% |
| 10% | * | * | * | * |

*can not be dissolved.

As is seen from the above, D,L-lactic acid effects a significant reduction in drying time over a range of from about 5% to about 20% by weight and achieves this result without any significant increase in viscosity. L-lactic acid, on the other hand, while reducing the drying time somewhat at 5% and 20% (but not at 10% or 15%) significantly increases the viscosity of the final product. The same is true of malic acid, citric acid, and L-tartaric acid. In fact, compositions above 15% of citric acid and above 5% of L-tartaric acid could not be prepared since the material does not even dissolve in collodion formulation.

What is claimed is:

1. In a fluid collodion composition for topical application in which nitrocellulose is dissolved in an ether-alcohol solvent, the improvement which consists essentially of a quantity of D,L-lactic acid being dissolved in said composition, said quantity being at least sufficient to decrease the drying time of said composition without significantly increasing the viscosity of said composition.

2. The improved collodion composition according to claim 1 wherein the amount of D,L-lactic acid is from about 5% to about 20%.

3. The improved collodion composition according to claim 2 wherein the amount of D,L-lactic acid is from about 15% to about 20%.

4. The improved collodion composition according to claim 3 wherein the amount of D,L-lactic acid is from about 16% to about 17%.

5. The method of decreasing the drying time of a fluid collodion topical composition in which nitrocellulose is dissolved in an ether-alcohol solvent without significantly increasing viscosity which consists of incorporating in said composition from about 5% to about 20% by weight of D,L-lactic acid.

* * * * *